United States Patent [19]

Papageorgiou

[11] 4,282,250

[45] Aug. 4, 1981

[54] REMEDY FOR SKIN INJURIES AND DISEASES

[76] Inventor: Vassilios P. Papageorgiou, Angelaki 33, Thessaloniki, Greece

[21] Appl. No.: 867,532

[22] Filed: Jan. 6, 1978

[30] Foreign Application Priority Data

Jan. 7, 1977 [DE] Fed. Rep. of Germany ....... 2700448

[51] Int. Cl.³ ............................................. A61K 31/22
[52] U.S. Cl. ................................... 424/311; 424/314; 560/185; 560/221; 560/255
[58] Field of Search ................ 424/311, 314; 560/185, 560/221, 255

[56] References Cited

PUBLICATIONS

Tobato et al., Chemotherapy 62(4), 18482 (1976).
Merck Index, 8th ed., p. 32 (1968).
Inagaki et al., Chem. Abst. 69:41955h (1968).
Shukla et al., Chem. Abst. 75:126532s (1971).
Kyogoku et al., Chem. Abst. 80:52315c (1974).
Futagoishi et al., Chem. Abst. 78:128376e (1973).
Morimoto et al., Chem. Abst. 64:12617e (1966).

Primary Examiner—Leonard Schenkman
Attorney, Agent, or Firm—Fleit & Jacobson

[57] ABSTRACT

The present invention provides a composition suitable for external application against skin injuries and diseases, such as ulcera, [e.g., *Ulcus Cruris* (indolent leg ulcer)], burns, scalds, open skin wounds, and the like, and having as its active ingredient a compound of the general formula

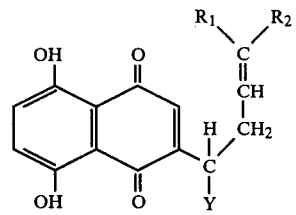

wherein Y is hydrogen or —OX in which X represents hydrogen, a carboxylic acid residue, or a derivative of a carboxylic acid residue, and $R_1$ and $R_2$ are alkyl groups, e.g., lower alkyl groups such as methyl, and mixtures of these compounds. The most active of these ingredients is the compound of the above formula wherein X is the acetyl ester of the 3-methyl-3-hydroxy-butanecarboxylic acid residue. When mixtures of compounds including said most active compound of said general formula are employed against the aforesaid skin injuries and diseases, a synergistic effect is obtained. The compounds are preferably applied in admixture with a carrier, particularly in the form of a lipophil ointment, which, in addition to triglycerides, such as olive oil, also contains a wax, e.g., beeswax, and/or a vegetable gum, e.g., mastix. The invention also contemplates the extraction of the active compounds from the plants in which they occur at a temperature not exceeding about 80%, preferably not exceeding about 40° C., and in the substantial absence of light and oxygen, i.e., in substantial darkness and in an inert atmosphere, such as nitrogen.

17 Claims, No Drawings

REMEDY FOR SKIN INJURIES AND DISEASES

The present invention is concerned with a composition, preferably in the form of an ointment, for external treatment of skin injuries and diseases, e.g., ulcera [such as *Ulcus cruris* (indolent leg ulcer)], burns, wounds, or the like, and which has been found, surprisingly, to be therapeutically successful even in different cases, as for example, in the case of *Ulcus cruris*, the most persistent of all skin ulcera.

The inventive composition contains, as its active ingredient, a compound of the following general Formula I:

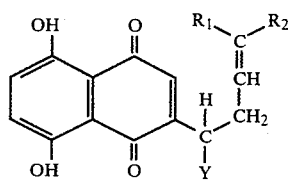

FORMULA I wherein Y is hydrogen or —OX in which X represents hydrogen, a carboxylic acid residue, or a derivative of a carboxylic acid residue, and $R_1$ and $R_2$ are alkyl groups, e.g., lower alkyl groups such as methyl, and mixtures of these compounds.

The most active of these compounds is the hitherto unknown compound of the above Formula I wherein Y is —OX and in which X is the acetyl ester of the 3-methyl-3-hydroxybutanecarboxylic acid residue, this most active compound being represented by the following Formula II:

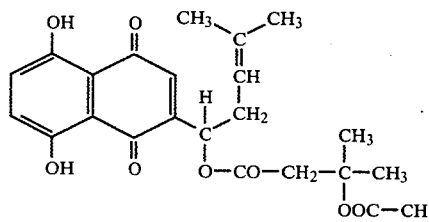

FORMULA II

The preparation of this compound is described hereinafter.

It has been found that by making various other substitutions in the above general Formula I compounds are obtained which are also effective against the said skin injuries and diseases. Some substitutions result in substances known to be contained in various plants belonging to the family of Boraginaceae, such as the dextrarotatory alkannin of the following Formula III:

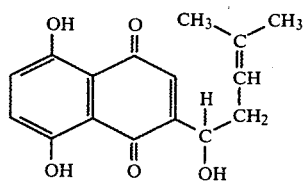

FORMULA III or its optical isomer, the levorotatory shikonnin, or the β,β'-dimethylacrylic ester of said alkannin and which has the following Formula IV:

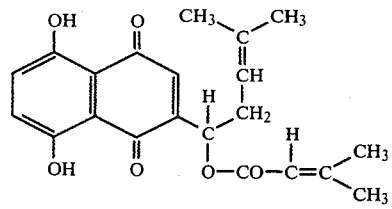

FORMULA IV

Although the healing effluency of these latter substances is definitely inferior to that of the compound represented by Formula II when these substances are used alone, a synergistic effect is obtained when they are combined with the compound of Formula II or other similarly highly effective substances to be described hereinafter. Alkannin can be obtained from *Alkanna tinctoria* by extraction with alcohol and/or ether in the form of an intensively red, fat-soluble dyestuff. Today, it is principally used for dreing food and lipsticks, after having been replaced as a dye for wool and silk by less expensive dyes. In antiquity, the unextracted alkanet root was used with oil and grease as make-up and later, particularly because of its tanning content, as an astringent for diarrhea and externally for wound treatment, skin diseases, etc. These types of use have long since been discontinued because better and less expensive tanniferous substances are available for the purpose of these applications. Another plant containing alkannin and belonging to the same plant family is *Arnebia noblis* for which no other physiological or pharmaceutical effect, except for a certain antibiotic effect, is known, other than the fact that its ether extract allegedly has an antitumor effect.

Among the known plants containing shikonnin, the *Lithospermium erythrorhizon* should be mentioned, which, it is suspected, could be effective for light cases of *Acne vulgaris* and eczema, as well as *Jatropha glandulifera*, which is used in popular medicine as a lenitive for rheumatic pain among Hindus.

None of these known pharmaceutical effects and possibilities of use of plants containing alkannin or shikonnin, could have presupposed or predicted the surprising finding in accordance with this invention, i.e., that the dyestuff alkannin, its β, β'-dimethylacrylic ester or shikonnin, or mixtures of these known substances, would show good therapeutic results of the aforesaid skin injuries and diseases, and they could have presupposed even less than the newly found compound represented in Formula II even exceeds by far the known compounds with regard to its therapeutic effect.

Other substitutions in Formula I result in hitherto unknown substances, all of which show not only a synergistic effect, but also a therapeutic effect comparable to that of the compound of Formula II, i.e., some of them are only slightly less and others even more effective than said compounds of Formula II. Such substances, which have been prepared and found effective in the aforesaid sense by clinical testing are defined by Formula I in which $R_1$ and $R_2$ are both methyl and Y represents:

| | |
|---|---|
| —OCOCH$_2$CH(CH$_3$)$_2$ (Isovaleric ester of alkannin) | FORMULA V |
| —H (Desoxy alkannin or desoxy shikonnin) | FORMULA VI |
| —OCOCH$_3$ (acetylester of alkannin or shikonnin) | FORMULA VII |

| | |
|---|---|
| —continued | |
| —OCOCH(CH₃)₂<br>(Isobutylester of alkannin or shikonnin) | FORMULA VIII |
| —OCOCH₂—C—(CH₃)₂<br>　　　　　\|<br>　　　　　OH<br>(β-hydroxy-isovaleryl shikonnin) | FORMULA IX |
| —OCO—CH—CH₂—CH₃<br>　　　　\|<br>　　　　CH₃<br>(α-methyl-η-butylester of alkannin or shikonnin) | FORMULA X |
| —OCOC=CHCH₃<br>　　　\|<br>　　　CH₃<br>(angelic ester of alkannin or shikonnin) | FORMULA XI |
| —OCOCH₂C(CH₃)₂OCOCH₃<br>(β-alkoxy-isovaleryl ester of alkannin or shikonnin) | FORMULA XII |

The preparation of the compounds of Formulas V and XI are described hereinafter.

While further developing the invention, it was found that a mixture of various compounds of the aforementioned generic Formula I, which mixture is quite effective for the aforesaid skin injuries and diseases, can be obtained by extraction from a plant source, such as the plant itself or plant parts, containing alkannin and/or shikonnin with lipophil organic solvents, such as alcohol, ether, and acetone, with or without the addition of a given amount of water, or with liquid fats, such as olive oil, provided that during the entire process of producing the extract, i.e., during extraction as well as during the subsequent concentration of the extract obtained, if concentration is indeed indicated, the temperatures must be carefully maintained below those normally used during production of known plants extracts destined for conventional application purposes, particularly as a dyestuff or dye solution obtained by extraction from plants containing alkannin. According to the invention, a temperature of 80° C. must absolutely not be exceeded. It is useful to keep the temperature distinctly below that limit, i.e., not above 50° C. and preferably not above 40° C.

It was found that at higher temperatures, the compounds of said general Formula I contained in the natural materials polymerized relatively quickly, thus essentially decreasing their therapeutic effect on the aforesaid skin injuries and diseases or, if polymerization is too extensive, completely destroying it.

It was found further, that it is advantageous to avoid not only elevated temperatures, but also the presence of oxygen and light during the extraction and also during the possible subsequent concentration of the extract; for example, by performing the extraction, and possible concentration, in darkness in a nitrogen atmosphere.

In addition, it was found that plant extracts carefully produced by this method had, in addition to the therapeutic effect according to the invention for the aforesaid skin injuries and diseases, also a distinct fungicidal and bactericidal action, e.g., on *staphylococcus aureus* and *staphylococcus epidermis*, as well as *candida albincans*.

The effectiveness of the thus produced plant extracts on the aforesaid skin injuries and diseases can be further increased by additionally incorporating the compound of Formula II therein; but even without such addition they are considerably more effective than all other remedies known, and so far used, for the aforesaid skin injuries and diseases, particularly for the treatment of *Ulcus cruris*.

It was further found that the active substances, according to this invention, develop their effectiveness best in a lipophil ointment base; in particular, in a base which, in addition to triglycerides, such as olive oil, soy oil, or the like, also contains waxes, e.g., beeswax and/or vegetable gum, such as mastix, cherry gum, or the like. The further addition of Vaseline to the ointment base does not result in any additional therapeutic advantage but may be advisable in certain cases for manufacturing and/or technical reasons.

The contents of the above active substances in the ointments, according to the invention, should be about from 0.01 to 3%, by weight, preferably approximately 0.1 to 0.5%, by weight.

The pure compound of Formula II is prepared as follows:

100 g powdered dry roots of *Alkanna tinctoria* were extracted with 400 ml n-hexane in an inert (nitrogen) atmosphere at room temperature and stirred magnetically for 1 h. The extraction was repeated thrice. The combined extract upon evaporation of the solvent afforded 4.8 g of red solid residue. Yield 4.8%.

The residue was dissolved in n-hexane and its components were isolated by preparative TLC. The plates, 20×20 cm, were covered with an emulsion consisting of 120 g Kieselgel type 60 (Merck) and 240 ml distilled water to form a layer 0.5 mm thick. The plates were activated for 30 min. at 110° C. The solution was applied as a band 16×0.3 cm and the plates were developed for 14 cm using the mixture benzene-chloroform-acetone (50:50:1) as mobile phase.

The solvent was evaporated in a stream of nitrogen and the red band 3 was scraped off. The powder thus obtained was treated with acetone and filtered. Evaporation of acetone afforded 0.015 g of 3-methyl-3-acetoxy-butanoic ester of alkannin (β-acetoxy-isovaleric ester of alkannin).

The pure compounds of Formulas V and XI are prepared as follows:

The residue from a hexane extract of the dried roots of *Alkanna tinctoria* was extracted with methanol. From the methanol solution the esters of Formula V and XI were obtained as insoluble Cu-complexes by the addition of $(CH_3COO)_2Cu$. The Cu-complexes were decomposed with 10% HCL, to give a mixture of free pigments. The mixture of the pigments was fractionated on silica gel columns to give separated pigments V and XI.

The isovaleric ester V, melting point 104°–105° C., corresponds to the formula $C_{21}H_{24}O_6$ (Analysis calculated: 67.74% C; 6.45% H; 25.18% O—Found: 67.87% C; 6.39% H; 25.57% O.) The angelic ester XI (deep red oil) corresponds to the formula $C_{21}H_{22}O_6$ (Analysis calculated: 68.10% C; 5.94% H; 25.96% O—Found: 68.12% C; 6.01% H; 25.35% O).

The structure elucidation for both above mentioned esters V and XI was based on the spectral data of UV, visible and IR spectra, NMR, and mass spectroscopy.

The following example illustrates the production of the composition of the invention in the form of an ointment and its clinical testing against Ulcus cruris.

EXAMPLE I (a) Method of production 1.25 kg of powder from the root of Alkanna tinctoria, in accordance with the specification of the British Pharmaceutical Codex 1949, having a grain size of 90% <25 mesh was extracted twice, each time with 3.8 kg olive oil while stirring at 40° C. in an $N_2$ atmosphere and in the substantial exclusion of light. The extract was centrifugated and subsequently bright filtered at from 30° to 40° C.

According to this method, approximately 50 g of extract was obtained which corresponds to a yield of 4% with regard to the amount of *Alkanna tinctoria* roots used. This extract contained approximately 40%, or 20 g, of tinctoria waxes and 60%, or 30 g, of compounds of the general Formula I. When the working method described is followed exactly, in particular, when an increase of the temperature to above 40° C. and the presence of oxygen and effect of light are avoided, only an increasingly small portion of these 30 g consists of the known alkannin, while from more than 95% to in excess of 99% consists of compounds of Formulas II and IV, which, in contrast to the known alkannin, display the surprisingly good therapeutic effect on *Ulcus cruris*.

To the thus-obtained olive oil extract is added a mixture of 1.6 kg of beeswax and 0.75 kg of mastix, while stirring, and it is homogenized until it returns to ambient temperature.

(b) Clinical Testing

In the clinic, a total of 52 stationary cases (38 women and 14 men) of *Ulcera cruris* in the presence of Varicosis were treated with the ointment produced according to the above method and the effect was evaluated by means of the healing process.

These stationary cases were exclusively cases of Ulcera which showed a poor or delayed healing tendency due to induration of connective tissue of the surrounding area or due to a deficient vascular supply. The test ointment was applied once a day on the Ulcera, while treatment of the surrounding area of the ulcer, e.g., covering by neutral pastes, was continued. The healing process was checked during the daily change of the dressing.

Where treatment with the ointment took place, the majority of the cases showed clearing up of the ulcer base and disappearance of the light wound coating. During the following two weeks, one could observe the beginning of good wound granulation, which is an essential step forward in the healing process. Simultaneously, a distinctly increasing epithelization of the ulcer edges occurred, and thus, in the vast majority of cases treated (41 cases or about 78%), an improved healing tendency could be observed. During the further healing process, generally clean and smooth wound conditions could be recorded which resulted in healing up, or at least expensive improvement, of the Ulcera in a period of from 5-6 weeks. The test ointment for treatment of Ulcera cruris therefore proved to be of particular advantage due to the improvement of the wound granulation and tendency to ephithelization. In the remaining 11 cases, the treatment with the test ointment—as well as the previous therapy with other local therapeutics—had little effect due to a deficient vascular supply or scarred induration.

EXAMPLE II (a) Preparation of Ointment

An ointment containing a mixture of the isovaleric ester of Formula V and the $\beta,\beta'$-dimethylacrylic ester of Formula IV in equal quantities, i.e., 0.5% by weight of each, or 1.0% by weight together, in olive oil was prepared. The preparation conditions were the same as of the preparation of the ointment of Example 1 containing the extract of *Alkanna tinctoria*.

(b) Clinical Study

The study was held on a group of 72 patients, all of whom suffered from *Ulcus cruris* on the lower part of the leg. The healing results obtained with this ointment, which was free of the other accompanying compounds contained in the ointment of Example 1, although still quite satisfactory, was slightly inferior to those of Example 1. The number of successes was 54, corresponding to 75%.

EXAMPLE III

To the ointment of Example II, the compound of FORMULA XII was added in equal quantity, so that each of the compounds V, IV and XII was present in a concentration of ⅓% or 1% together. The percentage of successes was 82%.

EXAMPLE IV

Dried roots of *Macrotomia Chefalotes* were extracted at room temperature with n-hexane. The extract was then extracted with methyl alcohol, the methyl alcohol evaporated and the residue again extracted with n-hexane.

After evaporation of the n-hexane, the residue was extracted with aqueous NaOH, the alkali extract acidified and again extracted with n-hexane. The mixture of pigments constituting this extract after evaporation of the hexane was used to prepare several ointments with different carriers, each of them containing 1% of said mixture of pigments. All ointments, of which the carrier was a fatty substance such as corn oil, soy bean oil and olive oil, showed good healing properties—the ointment with olive oil as carrier having slightly better properties than the other ones. However, the curative action of the pigments was diminished when a non-fatty carrier, the polysorbate Tween 80, was used.

What is claimed is:

1. A composition suitable for external application for healing open wounds, including Ulcus cruris, comprising as its essential active ingredient from about 0.01–3% by weight of at least one compound of the general formula:

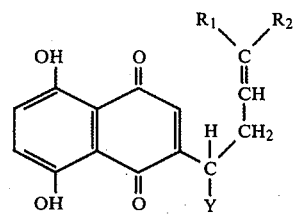

wherein Y is —OX in which X represents

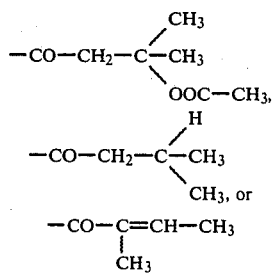

and $R_1$ and $R_2$ are methyl and a suitable carrier.

2. The composition of claim 1 wherein Y is —OX and in which X is the group:

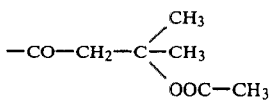

3. The composition of claim 1 wherein Y is —OX and in which X is the group:

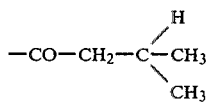

4. The composition of claim 1 wherein Y is —OX and in which X is the group:

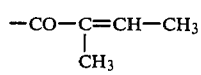

5. The composition of claim 1 wherein the essential active ingredient comprises a mixture of the compounds of claims 2, 3 or 4.

6. The composition of claim 1 wherein the carrier is a lipophilic ointment containing a mixture of triglycerides and at least one member selected from the group consisting of a wax and a gum.

7. The composition of claim 6 wherein the triglycerides are derived from a vegetable oil.

8. The composition of claim 7 wherein the vegetable oil is olive oil.

9. The composition of claim 7 wherein the vegetable oil is soybean oil.

10. The composition of claim 6 wherein the wax is beeswax.

11. The composition of claim 6 wherein the gum is mastix.

12. The composition of claim 1 wherein the essential active ingredient is present in the composition in the amount of about from 0.1 to 0.5% by weight.

13. A method for the treatment of open wounds, including Ulcus cruris, comprising applying to said open wounds to improve wound granulation and epithelization and healing thereof, a composition having as its essential active ingredient from about 0.01–3% by weight of at least one compound of the general formula:

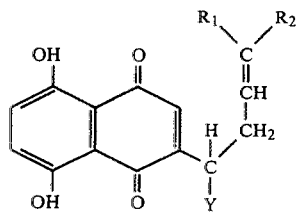

wherein Y is —OX in which X represents

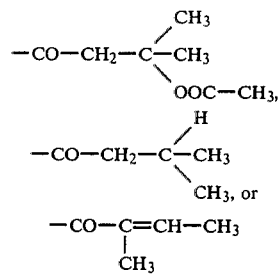

and $R_1$ and $R_2$ are methyl.

14. A method for the therapeutic treatment of Ulcus cruris comprising applying to the ulcer an effective amount of the composition of claim 1 to improve the healing thereof.

15. A method for the therapeutic treatment of Ulcus cruris comprising applying to the ulcer an effective amount of the composition of claim 2 to improve the healing thereof.

16. The method for the therapeutic treatment of Ulcus cruris comprising applying to the ulcer an effective amount of the composition of claim 5 to improve the healing thereof.

17. The method for the therapeutic treatment of Ulcus cruris comprising applying to the ulcer an effective amount of the composition of claim 4 to improve the healing thereof.

* * * * *